United States Patent [19]

Blunck

[11] 4,248,598
[45] Feb. 3, 1981

[54] PROCESS AND APPARATUS FOR THE DETERMINATION OF THE CONTENTS OF ORGANICALLY BOUND CARBON IN WATER CONTAINING ORGANIC SUBSTANCES AND A HIGH CONCENTRATION OF SALTS

[76] Inventor: Otto H. Blunck, Schrötteringksweg 11, 2000 Hamburg 76, Fed. Rep. of Germany

[21] Appl. No.: 42,888

[22] Filed: May 29, 1979

[30] Foreign Application Priority Data

May 30, 1978 [DE] Fed. Rep. of Germany ....... 2823587

[51] Int. Cl.³ .................. G01N 31/12; G01N 33/18
[52] U.S. Cl. ........................... 23/230 M; 23/230 R; 23/230 PC; 422/78; 422/80
[58] Field of Search .......... 23/230 M, 230 PC, 230 R; 422/78, 80

[56] References Cited

U.S. PATENT DOCUMENTS 3,958,941  5/1976  Regan ................................. 422/80
4,095,951  6/1978  DiCola et al. .............. 23/230 PC X

*Primary Examiner*—Barry S. Richman
*Attorney, Agent, or Firm*—Roylance, Abrams, Berdo & Farley

[57] ABSTRACT

A process and apparatus for the determination of the organically bound carbon content in water containing organic substances and a high concentration of salt. This is accomplished by exposing a water sample that is to be analyzed to ultraviolet radiation until the entire carbon content contained in the organic substances has been oxidized photochemically into $CO_2$. The amount of $CO_2$ thus developed is analyzed quantitatively as a measure of the content of organic substances and, thus, of the organically bound carbon contained in the water. Every water sample to be analyzed is inserted into an aqueous reaction medium which is free of carbon and which is essentially free of salt.

9 Claims, 1 Drawing Figure

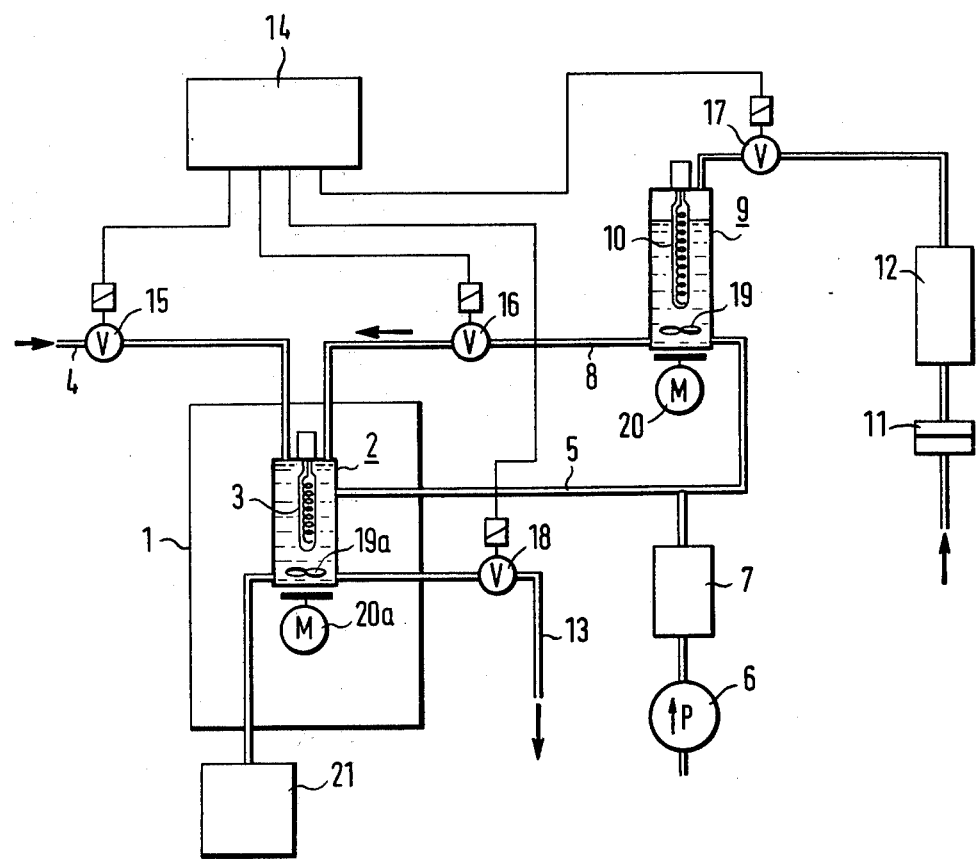

PROCESS AND APPARATUS FOR THE DETERMINATION OF THE CONTENTS OF ORGANICALLY BOUND CARBON IN WATER CONTAINING ORGANIC SUBSTANCES AND A HIGH CONCENTRATION OF SALTS

This invention relates to a process and apparatus for the determination of the organically bound carbon content in water containing organic substances and a high concentration of salts.

Many waters which are to be monitored analytically have very high concentrations of salt, for example, in the form of NaCl from the clarification plants of certain chemical factories (chlorine-alkali-plants). The salt concentrations in these waters may reach values up to 10% by weight. Frequently, the organic carbon content of these waters must be monitored continuously since the clarified water is to be recycled into the operation and large concentrations of organic carbon interfere considerably with the operation of the plant. Simultaneously, the so-called TOC- or DOC-values are monitored continuously whereby the value of the content of the entire organic carbon (TOC=total organic carbon) or the value of the contents of dissolved organic carbon (DOC=dissolved organic carbon), are determined. The TOC value differs from the DOC value by the POC value which represents the value of the content of particulate organic carbon (POC=particulate organic carbon). Higher concentrations of carbon may occur for example in the case of break-throughs of sludge in sewage plants.

Known apparatuses are not suitable for the continuous determination of the contents of organic impurities in water because of the high concentration of salt in the water. Thus, in one type of known apparatus, the water that is to be monitored is thermally treated at high temperature in a furnace heated to about 900°–1000° C. The carbon components contained in the water are quantitatively oxidized to $CO_2$, and the $CO_2$ thus produced is analyzed quantitatively. In such an apparatus, the combustion crucible of the heated furnace is encrusted within hours, whenever the water to be examined has a high salt content, because of the high salt concentration in the water, so that continuous measurements or examinations without time-consuming maintenance work are not possible.

In another type of known apparatus, the organic substances are oxidized photochemically to $CO_2$ in an acidic aqueous medium by treatment with ultraviolet (UV) radiation in the presence of an oxygen containing gas. In such an apparatus, the photochemical oxidation of the organic substances is impeded by the chlorine ions. When the salt concentration is in the order of about 10%, a one-time feed-in of a sample of 500 $\mu l$ is sufficient in order to disturb or even prevent the photochemical oxidation process during the next analysis cycle.

It is an object of this invention to provide a process and an apparatus for the determination of the content of organically bound carbon in water containing a high concentration of salt in which use is made of a photochemical oxidation utilizing ultraviolet radiation in which the disadvantages previously discussed with respect to prior art apparatuses are not encountered.

The object of this invention is attained by the process and apparatus schematically illustrated in the accompanying drawing. More particularly, there is provided a process and apparatus for the determination of the organically bound carbon content in water containing organic substances and a high concentration of salt. This is accomplished by exposing a water sample that is to be analyzed to ultraviolet radiation until the entire carbon content contained in the organic substances has been oxidized photochemically into $CO_2$. The amount of $CO_2$ thus developed is analyzed quantitatively as a measure of the content of organic substances and, thus, of the organically bound carbon contained in the water. Every water sample to be analyzed is inserted into an aqueous reaction medium which is free of carbon and which is essentially free of salt.

The practice of this invention permits one to execute continuously one measuring cycle after another without the necessity for special cleaning and maintenance work, since at the end of each measuring cycle, the entire mixture consisting of the preceding water sample and the aqueous reaction medium used in connection with it is eliminated from the system and is exchanged for a mixture consisting of a new water sample and a new aqueous medium for the next measuring cycle. As a result of the continuous execution of measurements or analyses, there will be no increase of the salt concentration in the aqueous reaction medium and in the analysis vessel containing the reaction medium, thus eliminating the danger of encrustation with salt which would impede or even prevent the photochemical oxidation. Thus, the practice of this invention creates the possibility for full automatization of the measuring cycles to be carried out successfully, which measuring cycles require time periods of essentially unchanged duration. After each constant time period, a new and accurate analysis of the water sample which is to be clarified and analyzed is obtained.

Referring more specifically to the drawing, the apparatus consists of a customary, known DOC measuring device 1 which, besides other construction units not shown, contains an irradiation vessel or receiving vessel 2 for the water sample to be analyzed. Inside the receiving vessel 2 is a UV light 3. The receiving vessel 2 is partially filled with an aqueous reaction medium which is free of carbon. The water sample to be analyzed is passed to the vessel 2 via the line 4. Air, from which $CO_2$ components have first been removed in an absorber 7, is fed by way of line 5 to the vessel 2. The pump 6 forces the air to pass through the line 5. This air flushes out any inorganically bound carbon prior to the actual measuring. Further, the air supplies oxygen for the oxidation and, finally, it also acts as the carrier gas in which gaseous $CO_2$ produced during the oxidation is carried to a known $CO_2$-measuring means 21 of the DOC measuring device 1.

Since the organic components contained in the water sample introduced via line 4 are converted quantitatively to $CO_2$ and are removed, there will be no residual carbon components in the aqueous reaction medium following irradiation.

In accordance with prior art processes in which fresh samples of water to be analyzed are introduced into the same aqueous reaction medium, when the samples of water to be analyzed contain a high concentration of salt, the concentration of the salt in the aqueous reaction medium becomes greater with each new sample. As a consequence, the time required for the complete oxidation of the organic substances becomes longer with each sample. If one plots the quantity of $CO_2$ produced as a function of time, there results a curve which at first rises, passes through a maximum and then drops again to zero. With an increasing concentration of salt in the reaction medium, this curve becomes broader and flatter. The expired time for a measuring cycle at the same time increases to a multiple of the original value until the curves are finally so broad and flat that an analysis is no longer possible and a treatment of the aqueous reaction medium becomes essential.

In accordance with the herein claimed invention, a new aqueous reaction medium is supplied via line 8 to the reaction vessel 2 for every new sample of water to be analyzed. The new aqueous reaction medium is precleaned while the current analysis is being conducted in a second irradiation vessel or water treatment vessel 9 with a second UV light 10. The reaction water, which may be taken for example from a tap water system, is precleaned in an ion exchanger 12 prior to entry into the processing vessel 9. The ion exchanger 12 may be preceded by a pressure reducer 11. A magnetic stirrer 19 may be provided to insure adequate turbulence in the reaction vessel 9. The magnetic stirrer 19 is driven by a motor 20. Similarly, a magnetic stirrer 19a and a motor 20a may be provided in the reaction vessel 2 to insure adequate mixing of the water sample with the aqueous reaction medium. Magnetic valves 15, 16, 17 and 18 are controlled by way of a control stage 14. The operation of the system will now be described.

Following completion of each cycle of analysis, the magnetic valve 18 is opened so that the contents of the reaction vessel 2 consisting of the aqueous reaction medium and the water sample which has been analyzed is discharged from the vessel 2 via line 13. After the contents of the reaction vessel 2 have been completely discharged, the valve 18 is closed and the valve 16 is opened. Fresh aqueous reaction medium free of carbon from vessel 9 is introduced into vessel 2 of the measuring device via line 8. When sufficient aqueous reaction medium has been received in vessel 2, valve 16 is closed and valve 17 is opened in order to admit a new charge of reaction water into the treatment vessel 9 after which the valve 17 is again closed. Finally, valve 15 is opened in order to feed a new water sample into the vessel 2 after which valve 15 is closed. Subsequently, oxygen containing gas, e.g., air, which is free of $CO_2$, is forced by means of pump 6 through the $CO_2$ absorber 7 via line 5 into the reaction vessel 2 which contains a mixture of aqueous reaction medium and the water sample to be analysed. The inorganically bound carbon of the water sample is first gased out after which the analyzing cycle begins. Simultaneously, air is fed from the absorber 7 to the processing vessel 9. As previously noted, the gas from the absorber 7 also serves as a carrier gas for $CO_2$ which is evolved during the oxidation reaction in the reaction vessel 2 for further transportation for the purpose of analysis.

I claim:

1. In a process for the determination of the content of organically bound carbon in water containing organic substances and a high concentration of salt which comprises exposing a sample of water that is to be analyzed to UV radiation until all of the carbon contained in the organic substances present in said sample have been oxidized photochemically into $CO_2$, and quantitatively measuring the amount of $CO_2$ thus developed, the amount of $CO_2$ thus developed being a measure of the content of organic substances and thus of the amount of organically bound carbon originally present in the sample water to be analyzed, the improvement which comprises inserting every sample of water to be analyzed into tap water which is free of carbon and which is essentially free of salt to form a reaction mixture, said tap water having been subjected to an ion exchange treatment to achieve freedom from salt after which an oxygen containing but $CO_2$-free gas is fed to the salt-free tap water to gas out any inorganically bound carbon present in said salt-free tap water, the tap water which is thus rendered salt free and free of inorganically bound carbon then being subjected to UV radiation until the entire organically bound carbon content which may be contained in said salt free and inorganically bound carbon free tap water is oxidized photochemically into $CO_2$, said introduced oxygen containing gas serving as a carrier gas to remove gaseous $CO_2$ developed during UV radiation;

conveying a gas containing oxygen to the resultant reaction mixture, said gas containing oxygen serving as a carrier gas to remove the gaseous $CO_2$ developed during the UV radiation step and to carry said $CO_2$ for quantitative $CO_2$ measurement;

exposing said reaction mixture to UV radiation to cause photochemical oxidation of the entire organically bound carbon content contained in said organic substances to $CO_2$; and removing said reaction mixture and replacing it with another sample of water to be analyzed and portion of tap water and repeating said improvement.

2. A process as defined in claim 1 wherein air is used as the gas containing oxygen, said air being subjected to an absorbing pretreatment to remove any $CO_2$ present prior to being fed to said reaction mixture.

3. A process as defined in claim 1 wherein a gas is fed to said reaction mixture causing inorganically bound portions of carbon which were present in said sample of water to be gassed out prior to exposing said mixture to UV radiation.

4. In an apparatus for the determination of the content of organically bound carbon in water containing organic substances and a high concentration of salt which comprises a container adapted to receive a sample of water that is to be analyzed and an aqueous reaction medium, means for introducing said water sample and said aqueous reaction medium into said container, means for removing said sample and reaction medium from said container, a UV radiator disposed in said container, means for introducing a gas containing oxygen into said container, means for discharging said introduced gas whereby said $CO_2$ evolved during UV radiation is carried out of the container to a means for quantitatively measuring the $CO_2$ evolved during UV radiation, and means for quantitatively measuring the $CO_2$ evolved during UV radiation, the improvement comprising utilizing tap water as the source of said aqueous reaction medium, said apparatus additionally comprising a purification vessel for the treatment of said tap water prior to its introduction into said container, a UV radiator being disposed in said vessel, an ion exchanger being provided for removing salt from said tap water prior to introduction into said vessel, means associated with said vessel for introducing a gas containing oxygen but free from $CO_2$ and means for discharging said introduced gas along with $CO_2$ evolved during UV radiation of the tap water in said vessel.

5. An apparatus as defined in claim 4 wherein the means for introducing a gas containing oxygen but free from $CO_2$ is in communication with a device for absorbing $CO_2$ from a gas.

6. An apparatus as defined in claim 5 wherein said $CO_2$ absorbing means is in communication with a gas pump.

7. An apparatus as defined in claim 6 wherein a valve is located in the means for introducing tap water into said purification vessel between said purification vessel and said ion exchanger.

8. An apparatus as defined in claim 7 wherein a motor driven stirrer is provided in said purification vessel.

9. An apparatus as defined in claim 8 wherein a pressure reducer is provided in said means for introducing tap water into said purification vessel preceding said ion exchanger.

* * * * *